US010945945B2

(12) United States Patent
Tomashevskaia et al.

(10) Patent No.: US 10,945,945 B2
(45) Date of Patent: Mar. 16, 2021

(54) STABILIZATION OF COSMETIC COMPOSITIONS COMPRISING FISH OILS AND HYDROXYLATED FATTY ACIDS AND/OR ITS DERIVATIVES

(71) Applicant: Conopco, Inc., Englewood Cliffs, NJ (US)

(72) Inventors: Marina Tomashevskaia, Trumbull, CT (US); Hasiba Bekto, Bristol, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 16/471,511

(22) PCT Filed: Dec. 12, 2017

(86) PCT No.: PCT/EP2017/082399
§ 371 (c)(1),
(2) Date: Jun. 19, 2019

(87) PCT Pub. No.: WO2018/114477
PCT Pub. Date: Jun. 28, 2018

(65) Prior Publication Data
US 2019/0328652 A1 Oct. 31, 2019

(30) Foreign Application Priority Data

Dec. 22, 2016 (EP) .................... 16206341

(51) Int. Cl.
| | | |
|---|---|---|
| *A61K 8/98* | (2006.01) | |
| *A61K 8/9789* | (2017.01) | |
| *A61K 8/06* | (2006.01) | |
| *A61K 8/34* | (2006.01) | |
| *A61K 8/36* | (2006.01) | |
| *A61K 8/362* | (2006.01) | |
| *A61K 8/37* | (2006.01) | |
| *A61K 8/46* | (2006.01) | |
| *A61Q 19/00* | (2006.01) | |

(52) U.S. Cl.
CPC ............. *A61K 8/987* (2013.01); *A61K 8/062* (2013.01); *A61K 8/347* (2013.01); *A61K 8/361* (2013.01); *A61K 8/362* (2013.01); *A61K 8/37* (2013.01); *A61K 8/375* (2013.01); *A61K 8/463* (2013.01); *A61K 8/9789* (2017.08); *A61Q 19/00* (2013.01)

(58) Field of Classification Search
None
See application file for complete search history.

(56) References Cited

U.S. PATENT DOCUMENTS

| | | | |
|---|---|---|---|
| 2,196,016 A | 2/1940 | Juehn | |
| 2,392,153 A | 1/1946 | Kastning | |
| 2,392,531 A | 8/1946 | Huehn | |
| 4,214,002 A | 7/1980 | Brandman et al. | |
| 4,288,464 A | 9/1981 | Smith | |
| 4,547,361 A | 10/1985 | Steltenkamp et al. | |
| 5,211,870 A | 5/1993 | Gilbert | |
| 5,472,705 A * | 12/1995 | Bruzzese ................. A61K 8/37 424/449 |
| 5,490,980 A | 2/1996 | Richardson | |
| 5,520,905 A | 5/1996 | Uhlmann et al. | |
| 5,650,157 A | 7/1997 | Bockow | |
| 5,871,762 A | 2/1999 | Venkitaraman et al. | |
| 5,919,440 A | 7/1999 | Kaiser | |
| 6,423,325 B1 | 7/2002 | Alaluf et al. | |
| 6,656,456 B2 | 2/2003 | Dodd et al. | |
| 6,663,854 B1 | 12/2003 | Shen | |
| 6,759,033 B2 | 7/2004 | Zimmerman et al. | |
| 6,782,307 B2 | 8/2004 | Wilmott et al. | |
| 6,884,409 B2 | 4/2005 | Klug et al. | |
| 7,667,057 B2 | 2/2010 | Regiert et al. | |
| 8,642,090 B2 | 4/2014 | Habich et al. | |
| 10,660,836 B2 * | 5/2020 | Pehratovic ............. A61Q 19/00 |
| 2003/0073771 A1 | 4/2003 | Sanders et al. | |
| 2003/0185865 A1 | 10/2003 | Jentzsch et al. | |
| 2003/0203009 A1 | 10/2003 | MacDonald | |
| 2004/0037792 A1 | 2/2004 | Hiramoto | |
| 2004/0048836 A1 | 3/2004 | Wilmott | |
| 2004/0147416 A1 | 7/2004 | Woo | |
| 2004/0213755 A1 | 10/2004 | Hochwalt | |
| 2005/0063928 A1 | 3/2005 | Withiam | |
| 2005/0118208 A1 | 6/2005 | Bewert | |
| 2006/0008533 A1 | 1/2006 | Habich et al. | |
| 2006/0099158 A1 | 5/2006 | Zander | |

(Continued)

FOREIGN PATENT DOCUMENTS

| | | |
|---|---|---|
| CN | 1334719 | 2/2002 |
| DE | 4042437 | 6/1992 |

(Continued)

OTHER PUBLICATIONS

Kanebo, "Skin moisturiser—has hydroxy ethane diphosphite, diethylenetriamine-5-acetate or L-ascorbic acid-2-phosphate, used f preventing skin chloasma or freckles", Derwent, Nov. 15, 1996, XP002197098; Abstract.
Co-pending U.S. Appl. No. 16/471,484.
Written Opinion 2 in PCTEP2017082399; dated Jan. 31, 2019.
Search Report and Written Opinion in PCTEP2017082399; dated Feb. 21, 2018.
LC-PUFA—A guide to health benefits and market trends; Health and Nutrition No. 1—a special supplement to inform; 2008; pp. 1-16 XP0055406787.
Search Report and Written Opinion in EP16206341; dated Oct. 5, 2017.
Dreher et al.; Hass Avocado Composition and Potential Health Effects; Critical Reviews in Food Science and Nutrition; 2013; pp. 738-750; XP002734320; vol. 53, No. 7; Taylor & Francis.

(Continued)

*Primary Examiner* — Ralph J Gitomer
(74) *Attorney, Agent, or Firm* — Stephanie Huang

(57) ABSTRACT

Stabilized skin care compositions are described. The compositions comprise a fish oil component that yields a product of oxidation and the component is stabilized with a radical scavenger, a peroxide decomposer and hydroxylated fatty acid and/or a derivative thereof.

10 Claims, No Drawings

(56) References Cited

U.S. PATENT DOCUMENTS

| | | |
|---|---|---|
| 2006/0135385 A1 | 6/2006 | Massaro |
| 2008/0203351 A1 | 8/2008 | Gao |
| 2008/0219938 A1 | 9/2008 | Grune |
| 2008/0311058 A1 | 12/2008 | Lou et al. |
| 2010/0183770 A1 | 7/2010 | Blanke et al. |
| 2013/0011455 A1 | 1/2013 | Blume |
| 2019/0380934 A1* | 12/2019 | Le Maire .............. A61K 8/361 |

FOREIGN PATENT DOCUMENTS

| | | |
|---|---|---|
| DE | 4320871 | 5/1996 |
| EP | 0003171 | 7/1979 |
| EP | 0003172 | 7/1979 |
| EP | 0063899 | 11/1982 |
| EP | 0147191 | 7/1985 |
| EP | 0306236 | 3/1989 |
| EP | 0404470 | 12/1990 |
| EP | 0974639 | 1/2000 |
| EP | 1321431 | 6/2003 |
| EP | 1419761 | 5/2004 |
| FR | 2741533 | 5/1997 |
| FR | 2968955 | 6/2012 |
| GB | 489769 | 8/1938 |
| GB | 2113090 | 8/1983 |
| JP | 55088677 | 7/1980 |
| JP | 60178810 | 9/1985 |
| JP | 01180818 | 7/1989 |
| JP | 8245335 | 9/1996 |
| JP | 10147512 | 6/1998 |
| JP | 2001 192328 * | 7/2001 |
| JP | 2001192328 | 7/2001 |
| JP | 2003192556 | 7/2003 |
| JP | 2003212712 | 7/2003 |
| JP | 2003527411 | 9/2003 |
| JP | 2004501068 | 1/2004 |
| JP | 10311585 | 9/2004 |
| JP | 2004290573 | 10/2004 |
| JP | 2005034365 | 2/2005 |
| JP | 2006045169 | 2/2006 |
| WO | WO9857619 | 12/1988 |
| WO | WO9318130 | 9/1993 |
| WO | WO9718320 | 5/1997 |
| WO | WO0108653 | 2/2001 |
| WO | WO0160331 | 8/2001 |
| WO | WO03045168 | 6/2003 |
| WO | WO03089020 | 10/2003 |
| WO | WO2005079740 | 9/2005 |
| WO | WO2006056283 | 6/2006 |
| WO | WO2006083387 | 8/2006 |
| WO | WO2006117055 | 11/2006 |
| WO | WO2008101852 | 8/2008 |
| WO | WO2010033034 | 3/2010 |
| WO | WO2016000863 | 1/2016 |

OTHER PUBLICATIONS

Search Report and Written Opinion in EP16206340; dated Oct. 11, 2017.

Sipernat 22S product Sheet; Evonik Industries 2004; Feb. 2004; p. 1-2 United States of America.

Rockwood Additives Limted/Rockwood Clay Additives GMBH; Laponite XLG; Jan. 1, 2003; p. 1; United States of America.

Magnesol Synthetic Magnesium Silicate; Magnesol; 2002; p. 1 The Dallas Group of America Inc; United States of America.

Yoshirhiro Shigeta; Current Status and Future Aspects for Odor Neutralizing Agents and Odor Removing Agents in Environments; Fragrance Journal; 1985; pp. 12-18 (Translation); No. 72 (vol. 13, No. 3).

IPRP2 in PCTEP2017082399; dated Apr. 1, 2019.

Written Opinion in PCTEP2017082399; dated Nov. 21, 2018.

Biochemical Reagents & Kits for Life Science Research; Sigma; 2006-2007; p. 1030 (2 pages); .; Sigma-Aldrich; United States of America.

Search Report and Written Opinion in PCTEP2016073552; dated Dec. 15, 2016.

Search Report and Written Opinion in PCTEP2017082400; dated Feb. 28, 2018.

IPRP2 in PCTEP2017082400; dated Apr. 10, 2019; World Intellectual Property Org. (WIPO).

Written Opinion 2 in PCTEP2017082400.

* cited by examiner

STABILIZATION OF COSMETIC COMPOSITIONS COMPRISING FISH OILS AND HYDROXYLATED FATTY ACIDS AND/OR ITS DERIVATIVES

FIELD OF THE INVENTION

The present invention is directed to a skin care composition, a method for stabilizing a composition comprising an ethyl ester of fish oil, and reducing malodor in a skin care composition. More particularly, the invention is directed to a skin care composition comprising radical scavenger, peroxide decomposer and hydroxylated fatty acid and/or its derivatives that are suitable to prevent formation of compounds that have been proven to yield offensively unpleasant odors in compositions, like lotions and creams. Such a scavenger, decomposer and hydroxylated fatty acid unexpectedly stabilize ethyl esters of fish oil in the skin care compositions and thereby minimize the formation of components that generate odors that are unacceptable to consumers. Moreover, such a scavenger, decomposer and hydroxylated fatty acid and/or its derivatives surprisingly do not negatively impact the desired sensory attributes resulting from the use of a skin care composition comprising the same, they allow for composition packaging in open and non-airless packages and preserve color of compositions highly desirable for use by consumers.

BACKGROUND OF THE INVENTION

A wide variety of skin care compositions tend to generate malodors after coming into contact with air, bacteria, skin or combinations of the same for prolonged periods of time. In fact, many skin care compositions comprise actives that, for example, oxidize, thereby generating volatile components that result in malodor. Fish oil ester containing compositions typically possess strong odors such that the odors often outweigh the consumer's desire to benefit from compositions comprising the same.

Attempts at reducing malodor in skin care compositions have been made. For example, fragrances have been used in skin care compositions to mask fish odors. Use of fragrances alone, however, is not always desirable since many consumers wish to use skin care compositions that are free of fragrances, due to various skin sensitivities and allergies. Also, fragrances within a product tend to have a shorter life than the product itself. Therefore, malodor masking may not be achieved during an entire product life.

Other attempts at reducing malodor in skin care compositions include using reduced amounts of components prone to oxidation and thus proven to be unstable in end use formulations. This approach is not advantageous because less component, often an active, is delivered to the consumer.

There is increasing interest to develop skin care compositions that have excellent sensory characteristics, are stable and free of malodor, and especially, skin care compositions that are free of malodor resulting from active decomposition, active that consumers are expecting to be present to yield a noticeable benefit when the skin care composition is applied. This invention, therefore, is directed to a skin care composition comprising radical scavenger, peroxide decomposer and hydroxylated fatty acid and/or its derivatives. The skin care composition made according to this invention is surprisingly free of malodor and discoloration originating from ethyl esters of fish oil that, for example, can oxidize in situ and produce by-products that negatively impact the quality.

Additional Information

Efforts have been disclosed for making cosmetic compositions. In World Application No. WO 93/18130, malodor personal cleansing bars with zeolite are described.

Other efforts have been disclosed for making cosmetic compositions. In U.S. Application No. 2006/0135385 A1, toilet bar compositions with pyran odor masking agents are described.

Still other efforts have been disclosed for making consumer product compositions with reduced odor. In European Patent Application No. EP 0063899 A2, fabric conditioning compositions whereby the same exhibit excellent deodorizing effects against a wide range of malodor ingredients.

Even other efforts have been disclosed for making cosmetic compositions. In Japanese Application No. JP 2004290573 A, deodorants having elasticity and flexibility are described whereby the same uses clay as a swelling agent. In U.S. Pat. No. 5,650,157, reducing odor of oil compositions is described. U.S. Pat. No. 5,472,705 describes pharmaceutical compositions with esters of omega 3 polyunsaturated acids.

None of the additional information above describes a skin care composition that has a radical scavenger, peroxide decomposer and hydroxylated fatty acid and/or its derivative that reduce malodor formation by preventing in situ breakdown a component comprising an ethyl ester of fish oil expected to deliver benefit to the consumer.

SUMMARY OF THE INVENTION

In a first aspect the present invention is directed to a composition comprising:
(a) a component comprising an ethyl ester of fish oil that can produce, in situ, a product of oxidation;
(b) a radical scavenger, peroxide decomposer and hydroxylated fatty acid and/or a derivative thereof;
(c) oil carrier; and
(d) water,
the composition being an emulsion wherein at least 90% by weight of the component comprising an ethyl ester of fish oil that can produce, in situ, a product of oxidation remains chemically stable, and free of aroma and discoloration for at least four weeks when the composition is maintained at a temperature of 45° C., the emulsion comprising from 0.1 to 1.5% by weight ethyl ester of fish oil.

In a second aspect the present invention is directed to a composition for application to skin comprising:
(a) a component comprising an ethyl ester of fish oil that can produce, in situ, a product of oxidation, the ethyl ester of fish oil being an ethyl ester of eicosapentaenoic acid, an ethyl ester of docosohexaenoic acid or a mixture thereof;
(b) a radical scavenger comprising pentaerythritol-tetrakis (3-(3,5-di-tertbutyl-4-hydroxyphenyl)propionate, peroxide decomposer comprising didocecyl 3,3'-thiodipropionate and hydroxylated fatty acid and/or a derivative thereof comprising glycerol monohydroxystearate;
(c) caprylic/capric triglyceride, high oleic sunflower seed oil, octylhydroxystearate, mineral oil, or a mixture thereof as oil carrier; and
(d) water,
the composition being an emulsion comprising from 0.1 to 1.5% by weight ethyl ester of fish oil.

In a third aspect, the invention is directed to a method for preventing malodor in a composition by suppressing aldehyde and/or ketone formation in the compositions of the first and second aspects of this invention.

In a forth aspect, the invention is directed to a method for making the compositions of the first and second aspects of this invention.

In a fifth aspect, the invention is directed to a cosmetic method of improving skin characteristics by contacting the skin with either the composition of the first or second aspects of this invention.

Additional aspects of the present invention will more readily become apparent from the description and examples which follow.

Skin, as used herein, is meant to include skin on the face, neck, chest, back, arms (including underarms), hands, legs, buttocks and scalp. Active, as used herein, is meant to include a component that improves a body characteristic after topical application like a skin characteristic and/or benefits the same wherein the active can be, and preferably is, an active in a cream, pump or aerosol spray, serum, lotion, balm, deodorant or gel. In an especially preferred embodiment, the composition of this invention is a leave-on composition and the active is an omega-3 ethyl ester of fish oil.

The active or component that can yield, in situ, a product of oxidation means an ethyl ester of fish oil that oxidizes to yield volatile compounds, such as low molecular weight (<C10) aldehydes and/or ketones which may include 1-pente-3-one, (Z)-4 heptanal, 1-octen-3-one, 2-4-heptadienal and the like. Remain chemically stable means at least 90% by weight of the component (based on total weight of the original total amount of component provided and as determined by HPLC using ASTM standards) remains intact and unoxidized in the composition for at least four weeks, and preferably, up to 8 weeks, and most preferably up to 12 weeks after composition with the component is stored at 45° C. in a non-airless pack for such respective amount of time and where active is present at 0.1 to 1.5% by weight in the emulsion. In a most preferred embodiment, the composition remains free of detectable fish aroma for up to 12 weeks after being stored at 45° C. and 3 months at room temperature in a non-airless pack (as determined by a skilled panelist). Remains chemically stable, as used herein, is synonymous with free of malodor and color change in that an offensive odor is not detected when product is used by a consumer and a color change is not detected upon visual inspection under such conditions such that the delta E (total color difference) is from 0.1 to 3 based on delta L*, a* and b* color differences taken on a Hunter Lab Colorimeter. Such malodor can be characterized as a "fish" odor such as those detected when trimethylamine is present. Radical scavenger means an agent suitable to neutralize free radical oxidation products. Peroxide decomposer, as defined herein, means an agent that breaks down lipid peroxides that result from fatty acid oxidation. Hydroxylated fatty acid means a fatty acid having at least one hydroxy group functionalization on its aliphatic backbone. A derivative of such hydroxylated fatty acid is meant to include an alcohol, and/or an ester thereof with a $C_2$-$C_6$ aliphatic group. Oil carrier means an oil other than the component that can produce, in situ, a product of oxidation.

Comprising as used herein is meant to include consisting essentially of and consisting of. Therefore, it is within the scope of this invention for the composition to consist essentially of or consist of a component that can produce, in situ, a product of oxidation, oil, radical scavenger, peroxide scavenger and hydroxylated fatty acid. Emulsion, as used herein, means oil-in-water emulsions.

Except in the Examples or where otherwise explicitly indicated, all numbers used herein, including those indicating amounts or ratios of materials, are to be understood as modified by the word "about". For the avoidance of doubt, weight percent of a component or ingredient in a composition is meant to be based on the weight percent of the final composition desired.

DETAILED DESCRIPTION OF THE PREFERRED EMBODIMENTS

Illustrative and non-limiting examples of the type of components that can produce, in situ, a product of oxidation and that may be used in this invention include polyunsaturated fatty acids comprising ethyl esters of fish oil. The desired fatty acids are omega-3 fish oils comprising ethyl ester of eicosapentaenoic acid, ethyl esters of docosahexaenoic acid or mixtures thereof. In a most desirable embodiment, the omega three fish oil is an ethyl ester of eicosapentaenoic acid, an ethyl ester of docosohexaenoic acid or a mixture. In another most desirable embodiment, a mixture is used and the weight ratio of ester of eicosapentaenoic acid to ethyl ester of docosohexaenoic acid is 1:2 to 2:1, preferably the mixture will contain 5 to 40%, and most preferably, 10 to 30% by weight more ethyl ester of eicosapentaenoic acid than ethyl ester of docosohexaneoic acid. The fish oils suitable for use in this invention are commercially available from suppliers like BASF, Originates and Sigma-Aldrich.

Typically, the amount of component that can produce, in situ, a product of oxidation that may be used in the oil-based composition of this invention is from 0.1 to 1.5%, and preferably, from 0.1 to 1.2%, and most preferably, from 0.1 to 0.75% based on total weight of the composition (emulsion).

With respect to the radical scavenger that may be used in this invention, the same is limited only to the extent that it is suitable for use to stabilize a topical composition as defined herein and can be used in the presence of a peroxide decomposer. Illustrative examples include dibutylhydroxytoluene, rosemary extract, pentaerythritol tetrakis (3-(3,5-di-tert-butyl-4-hydroxyphenyl)propionate), octadecyl 3-(2, 5-di-tert-butyl-4-hydroxyphenyl) propionate or a mixture thereof.

Typically, the amount of radical scavenger suitable for use in the composition of this invention is from 0.01 to 1.0%, and preferably, 0.05 to 0.7%, and most preferably, from 0.05 to 0.6%, based on total weight of the composition and including all ranges subsumed therein. In an often desired embodiment, from 0.05 to 0.2% by weight radical scavenger is used, based on total weight of the composition and including all ranges subsumed therein.

The peroxide decomposer that may be used in this invention is limited only to the extent that it is suitable for use to stabilize a topical composition as defined herein with a radical scavenger. An illustrative example includes didodecyl 3,3'-thiodipropionate. Typically, the peroxide decomposer makes up from 0.01 to 1.0%, and preferably from 0.15 to 0.7%, and most preferably from 0.02 to 0.5% by weight of the composition. Especially preferred is when from 0.03 to 0.07% by weight of the peroxide decomposer is used, based on total weight of the composition.

In a desired embodiment, the radical scavenger employed in this invention is pentaerythritol tetrakis (3-(3,5-di-tert-butyl-4-hydroxyphenyl)propionate), octadecyl 3-(2,5-d i-tert-butyl-4-hydroxyphenyl)propionate or a mixture thereof and the peroxide decomposer is didodecyl 3,3' thiodipropionate. In such desired embodiment, the radical scavenger to peroxide decomposer weight ratio if from 2:8 to 8:2, and preferably, from 3:7 to 7:3, and most preferably, from 6:4 to 4:6. These radical scavengers are made commercially available by BASF under the names Tinogard® TT and Tinogard® TS, respectively. The peroxide decomposer is made commercially available under the Tinogard® DA name, also by BASF. Most preferred radical scavenger and peroxide decomposer mixtures include rosemary extract and Tinogard® DA; Tinogard® TT and/or Tinogard® TS with Tinogard® DA, and dibutylhydroxytoluene and Tinogard® DA.

Regarding the hydroxylated fatty acids and/or derivatives thereof selected for use, the same is limited only to the extent that it is suitable for use with the radical scavenger and peroxide decomposer described for use in this invention. Often preferred for use are alcohols as well as glycerol esters of hydroxylated fatty acids. Illustrative examples include hydroxystearyl alcohol, glycerol monohydroxystearate, hydroxystearyl glucoside, ethyleneglycol monohydroxystearate, glycerylmonoricinoleate, glyceryl dihydroxystearate, glyceryldiricinoleate, mixtures thereof or the like. Also preferred is 12-hydroxystearic acid and/or its derivatives, either alone or in a mixture with other hydroxylated fatty acids and/or their derivatives. In an often preferred embodiment, glycerol monostearate and glyceryl monohydroxystearate are preferred for use as well as mixtures thereof, where the weight ratio when both are used is often 3:7 to 7:3, and preferably, 4:6 to 6:4, and most preferably, from 45:55 to 55:45 including all ratios subsumed therein. Such hydroxylated fatty acids are commercially available from suppliers like NatureChem and Seppic.

The total amount of hydroxylated fatty acid used in the composition of this invention is from 0.01 to 8%, and preferably, from 0.01 to 6%, and most preferably, from 0.1 to 4% by weight, based on total weight of the composition and including all ranges subsumed therein.

Cosmetically acceptable carriers suitable for use in this invention include water. Water is the most preferred additional carrier when the end use composition is an emulsion. Amounts of water may range from less than 5% to about 97%, and preferably, from about 5 to about 90%, and most preferably, from about 35 to about 80%, and optimally, from about 40 to about 75% by weight, based on total weight of the composition and including all ranges subsumed therein. Oil-in-water emulsions are especially preferred.

Other cosmetically acceptable carriers (oil carriers) suitable for use in this invention may include mineral oils, dioctyl ester, octylhydroxystearate, high oleic triglycerides (greater than 40%, and preferably, 60 to 80% monounsaturated oleic acid, like sunflower seed oil), silicone oils, synthetic or natural esters, and alcohols. Amounts of these materials may range from 0.01 to 50%, and preferably, from 0.01 to 20%, and most preferably, from 0.01 to 7% by weight of the composition, including all ranges subsumed therein.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, and preferably, from 4 to 5 silicon atoms.

Linear volatile silicone materials generally have viscosities of less than 5 centistokes at 25° C. while cyclic materials typically have viscosities of less than 10 centistokes.

Nonvolatile silicone oils useful as carrier material include polyalkyl siloxanes, polyalkylaryl siloxanes and polyether siloxane copolymers. The essentially nonvolatile polyalkyl siloxanes useful herein include, for example, polydimethylsiloxanes (like dimethicone) with viscosities of from 5 to 100,000 centistokes at 25° C.

An often preferred silicone source is a cyclopentasiloxane.

Among suitable esters are:
(1) Alkenyl or alkyl esters of fatty acids having 10 to 20 carbon atoms like octyl hydroxystearate, isopropyl isostearate, isononyl isonanonoate, oleyl myristate, oleyl stearate, and oleyl oleate;
(2) Ether esters—such as fatty acid esters of ethoxylated fatty alcohols;
(3) Polyhydroxy alcohol esters such as ethylene glycol mono- and difatty-acid esters, diethylene glycol mono and -difatty-acid esters, polyethylene glycol (200-6000) mono and -difatty-acid esters, propylene glycol mono and -difatty acid esters, polypropylene glycol monooleate, polypropylene glycol monostearate, ethoxylated propylene glycol monostearate, glyceryl mono and -difatty-acid esters, polyglycerol-polyfattyesters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene-sorbitan fatty acid esters;
(4) Wax esters such as beeswax, spermaceti, myristyl myristate, stearyl stearate; and
(5) Sterol esters, of which soya sterol and cholesterol fatty acid esters are examples thereof.

In an especially preferred embodiment, the oil used is a high oleic triglyceride, and especially a commercially available high oleic triglyceride that is algae sourced.

Emulsifiers may be present in the emulsion compositions of the present invention. Total concentration of the emulsifier may range from 0.1 to 40%, and preferably, from 1 to 20%, and most preferably, from 1 to 5% by weight of the composition, including all ranges subsumed therein. The emulsifier may be selected from the group consisting of anionic, nonionic, cationic and amphoteric actives. Particularly preferred nonionic actives are those with a $C_{10}$-$C_{20}$ fatty alcohol or acid condensed with from about 2 to about 100 moles of ethylene oxide or propylene oxide; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids and amides; and polyoxyethylene sorbitan as well as combinations thereof. Alkyl polyglycosides and saccharide fatty amides (e.g. methyl gluconamides) are also suitable nonionic emulsifiers.

Preferred emulsifiers include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof.

Preservatives can desirably be incorporated into the compositions of this invention to protect against the growth of potentially harmful microorganisms. Suitable traditional preservatives for compositions of this invention are alkyl esters of parahydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol 1,2-alkane diols (like 1-2-octanediol), methyl paraben, ethyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition, including all ranges subsumed therein. In a desired embodiment, a preservative mixture of phenoxyethanol and 1,2-octanediol is used, typically at a weight ratio of 6:4 to 4:6.

Thickening agents may optionally be included in compositions of the present invention. Particularly useful are the polysaccharides. Examples include starches, natural/synthetic gums and cellulosics. Representative of the starches are chemically modified starches such as sodium hydroxypropyl starch phosphate and aluminum starch octenylsuccinate. Tapioca starch is often preferred. Suitable gums include xanthan, *sclerotium*, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes cross-linked polyacrylates such as the Carbomers (Acrylates/$C_{10-30}$ alkyl acrylate crosspolymer), polyacrylamides such as Sepigel® 305 and taurate copolymers such as Simulgel EGO and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100.

Amounts of the thickener, when used, may range from about 0.001 to 5%, and preferably, from 0.1 to 2%, and most preferably, from about 0.2 to 0.5% by weight of the composition including all ranges subsumed therein.

Fragrances (including natural and/or synthetic) may optionally be included in compositions of the present invention. Each of these substances may range from 0.01 to 5%, and preferably, from 0.1 and 3%, and most preferably, from 0.15 to 1% by weight based on total weight of the composition. In an especially preferred embodiment, the fragrance is long-lasting, an enduring fragrance.

Conventional humectants may be employed in the present invention. These are generally polyhydric alcohol-type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.5 to 20%, preferably between 1 and 15% by weight of the composition.

Monoenoic fatty acid (i.e., monounsaturated fatty acid) may optionally be employed with the component that can produce, in situ, a product of oxidation. Illustrative examples include cis-4-decenoic, cis-9-decenoic, cis-5-lauroleic, cis-4-dodecenoic, cis-9-tetradecenoic, cis-5-teradecenoic, cis-4-tetradecenoic, cis-9-hexadecenoic, cis-6-octadecenoic, cis-9-octadecenoic, tr-9-octadecenoic, cis-11-octadecenoic, cis-9-eicosenoic, cis-11-eicosenoic, cis-11-docosenoic, cis-13-docosenoic, cis-15-tetracosenoic acid, derivatives thereof or mixtures thereof.

The preferred optional monoenoic fatty acids (or salts or esters thereof) suitable for use in this invention are cis-6-octadecenoic acid (i.e., petroselinic acid) cis- and/or tri-9-octadecenoic acid (oleic) whereby the same may be used alone, in combination with other monoenoic fatty acids and/or in combination with CLA and/or in combination with other active components defined herein, including sunflower seed oil. In another preferred embodiment, an ester of cis- and/or tri-9-octadecenoic acid is used, and especially, a triglyceride thereof.

If used, the amount of monoenoic acid used in the invention is typically 70% less, and preferably, 60% less, and most preferably, 50% less than the amount of polyunsaturated fatty acid (or ester or salt thereof) used, based on total weight of oil-based compositions and emulsions of this invention.

Compositions of the present invention may include skin benefit vitamins. Illustrative vitamins included Vitamin $B_2$, Vitamin $B_3$ (niacinamide), Vitamin $B_6$, Vitamin D and K. Derivatives of the vitamins may also be employed. Total amount of vitamins when present in compositions according to the present invention may range from 0.001 to 5%, preferably from 0.01% to 1%, optimally from 0.1 to 0.5% by weight of the composition, and most preferably from 0.01 to 3% by weight of the composition.

Another optional additive suitable for use in this invention includes creatine and its derivatives, taurates, mixtures thereof or the like. Such additives, when used, collectively make up from about 0.001 to about 5% by weight of the composition.

Desquamation promoters may be present. Illustrative are the alpha-hydroxycarboxylic acids, beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic and its derivatives, lactic and malic acids. Salicylic acid is representative of the beta-hydroxycarboxylic acids. Amounts of these materials when present may range from 0.01 to 5% by weight of the composition. Salicylic acid is often preferred for use from 0.03 to 1%, and preferably, from 0.05 to 0.6% by weight of the composition of this invention.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from yarrow, chamomile, licorice, aloe vera, grape seed, citrus unshui, willow bark, sage and thyme.

Also optionally suitable for use include materials like chelators (e.g., EDTA), opacifiers (like $TiO_2$, particle size from 50 to 1200 nm, and preferably, 50 to 350 nm), $C_{8-22}$ fatty acid substituted saccharides, lipoic acid, retinoxytrimethylsilane (available from Clariant Corp. under the Silcare 1M-75 trademark), dehydroepiandrosterone (DHEA) and combinations thereof. Amounts of these materials, when used, may range from 0.001 to 10%, preferably from 0.001 to 1% by weight of the composition.

Sunscreen actives may also be included in compositions of the present invention. Particularly preferred are such materials as octocrylene, ethylhexyl p-methoxycinnamate, available as Parsol MCX®, Avobenzene, available as Parsol 1789®, benzophenone-3, also known as Oxybenzone, octyl salicylate, and homosalate. Inorganic sunscreen actives may be employed such as microfine titanium dioxide, zinc oxide, polyethylene and various other polymers. Amounts of the sunscreen agents when present may generally range from 0.1 to 30%, preferably from 0.5 to 20%, optimally from 0.75 to 10% by weight.

Conventional buffers/pH modifiers may be used. These include commonly employed additives like sodium hydroxide, potassium hydroxide, hydrochloric acid, citric acid and citrate/citric acid buffers. In an especially preferred embodiment, the pH of the composition of this invention is from 4 to 8, and preferably, from 4.25 to 7.75, and most preferably, from 6 to 7.5, including all ranges subsumed therein.

The compositions of the present invention, when topically applied, are suitable to improve a variety of skin characteristics. This is particularly true since the components that can produce, in situ, products of oxidation are typically skin benefit actives. These actives can moisturize, reduce wrinkles, contribute to even skin tone and overall improve the elasticity of skin.

When making the compositions of the present invention, ingredients, including hydroxylated fatty acid and/or a derivative thereof, may be added and stirred under moderate shear to produce an emulsion. Typically heat (75 to 85° C.) is used in order to enhance emulsion formulation. In an especially preferred embodiment, the component comprising an ethyl ester of fish oil, carrier oil and radical scavenger are added as a premix to an already formed initial emulsion and when the initial emulsion has been cooled to 20 to 30° C. to produce a final emulsion. Typically from 10 to 90%, and preferably from 25 to 75%, and most preferably, from 30 to 70% by weight of the radical scavenger in the final emulsion is provided in the initial emulsion.

A wide variety of packaging can be employed to store and deliver the composition of this invention. Packaging is often dependent upon the type of personal care end-use. For instance, leave-on skin lotions and creams can be packaged in plastic containers with a cap/cover or an opening at a dispensing end covered by a closure. Suitable closures are screw-caps, non-aerosol pumps and flip-top hinged lids. Packaging for antiperspirants and deodorants may involve a container with a roll-on ball on a dispensing end. Alternatively these types of personal care products may be delivered in a stick composition formulation in a container with propel-repel mechanism where the stick moves on a platform towards a dispensing orifice. Surprisingly, the compositions of the present invention do not require airless packaging.

The following examples are provided to facilitate an understanding of the present invention. The examples are not intended to limit the scope of the claims.

Example 1

Components capable of producing, in situ, a product of oxidation, radical scavengers and peroxide decomposers were added to cosmetic emulsion bases as described below. The emulsions were prepared by mixing ingredients under conditions of moderate shear at atmospheric pressure. Temperature was maintained at about 80° C. until the emulsion bases were complete.

The following base compositions/emulsions were used to assess the benefits of the claimed invention.

| Emulsion Base 1 | |
| --- | --- |
| Ingredient | Weight % of Emulsion |
| Water | Balance |
| Disodium EDTA | 0.05 |
| Preservative | 0.2 |
| Glycerin | 10.0 |
| Polyacylate Thickener | 0.2 |
| Sodium Hydroxide | 0.2 |
| Stearic Acid (and) Stearamide AMP | 0.9 |
| Cetyl Alcohol | 0.5 |
| Glyceryl Monohydroxystearate | 3.0 |
| PEG-100 Stearate | 0.7 |
| Tinogard TT | 0.05 |
| Tinogard DA | 0.05 |
| Propylparaben | 0.1 |
| Tapioca Starch | 0.5 |
| Phenoxyethanol | 0.4 |
| Fragrance | 0.8 |

| Emulsion Base 2 | |
| --- | --- |
| Ingredient | Weight % of Emulsion |
| Water | Balance |
| EDTA | 0.05 |
| Titanium Dioxide | 0.2 |
| Methylparaben | 0.2 |
| Taurate Thickener | 0.15 |
| Glycerin | 4.0 |
| Tinogard TT | 0.05 |
| Tinogard DA | 0.05 |
| Xanthan Gum | 0.1 |
| Liquidum Parafinum | 1.0 |
| Cetearyl Alcohol, PEG-20 Stearate | 3.0 |
| Hydroxystearyl alcohol (85%) and Hydroxystearyl Glucoside (15%) | 2.0 |
| Glyceryl Monohydroxystearate | 3.0 |
| Propylparaben | 0.1 |
| Stearic acid | 1.0 |
| Cetearyl Alcohol | 1.0 |
| Niacinamide | 0.1 |

Example 2

Premix (fish oil, radical scavanger and carrier oil (high oleic >40%) sunflower seed oil was prepared with the amounts indicated below. Carrier oil was used at an amount to yield a final emulsion of 4% by weight sunflower seed oil. Each premix was added to the emulsions of Example 1.

| Fish Oil[1] Concentration, % | EPA/DHA Recovery, 12 Weeks at 45 C., % (HPLC) | Color[2] Change, delta E | GMHS in emulsion of Example 1 or as indicated | Tinogard TT 0.05%/ Tinogard DA 0.05% | Malodor at 12 Weeks, 45 C. in a jar | Malodor After Skin Application | Odor Profile[3] |
|---|---|---|---|---|---|---|---|
| 0.5 | >90 | <3 | Yes | Yes | No | No | Fragrance |
| 1 | >90 | <3 | Yes | Yes | No | No | Fragrance |
| 1 | >90 | >3 | Yes | No | Yes | Yes | Strong Fish Odor |
| 1 | >90 | >3 | No | Yes | Yes | Yes | Strong Fish Odor |
| 2 | >90 | <3 | Yes | Yes | No | No | Slight Mushroom Odor |
| 2 | >90 | >3 | No | Yes | Yes | Yes | Strong Fish Odor |
| 2 | >90 | <2 (with salicylic acid) | Yes | Yes | No | No | Slight Mushroom Odor |

[1]Omega 3 ethyl ester of Fish oil, ethyl esters of eicosapentaenoic acid (EPA) and docosohexaneoic acid (DHA), 2:1 ratio by weight, made available by BASF.
[2]Using a Hunter Lab Colorimeter
[3]Odor Detected (strong fish odor) via panelist analysis.

The data in the table above unexpectedly demonstrates that the strong fish aroma associated with compositions comprising fish oil can be suppressed when the same are formulated according to the present invention.

Example 3

An emulsion was made comprising the ingredients consistent with this invention.

| | |
|---|---|
| Water | 81.55 |
| 12-Hydroxystearic Acid | 1 |
| Glycerylmonostearate (GM$^s$) | 3 |
| Hydroxystearyl alcohol (85%) and Hydroxystearyl glucoside (15%) | 3 |
| Mineral Oil | 3 |
| PEG-100 Stearate | 2 |
| Higholeic sunflower seed oil | 3 |
| Fish Oil[1] | 1.5 |
| Tinogard TT | 0.05 |
| Tinogard DA | 0.05 |
| Phenoxyethanol | 0.4 |
| Preservative | 0.2 |
| Fragrance | 0.75 |

[1]As identified in Example 2

| EPA/DHA Recovery 12 Weeks at 45° C., % (HPLC) | Color Change Delta E | Malodor at 12 weeks, 45° C. in a jar |
|---|---|---|
| >90 | <3 | No |

All testing was performed as described in Example 2. The data in the table unexpectedly demonstrates that the strong fish aroma associated with compositions comprising fish oil can be suppressed when the same are formulated according to the present invention.

What is claimed is:

1. A composition for application to skin comprising:
   (a) a component comprising an ethyl ester of fish oil that can produce, in situ, a product of oxidation, the ethyl ester of fish oil being an ethyl ester of eicosapentaenoic acid, an ethyl ester of docosohexaenoic acid or a mixture thereof;
   (b) a radical scavenger comprising dibutylhydroxytoluene, pentaerythritol tetrakis (3-3,5-di-tertbutyl-4-hydroxyphenyl) propionate) or a mixture thereof;
   (c) peroxide decomposer comprising didocecyl 3,3'-thiodipropionate;
   (d) hydroxylated fatty acid, hydroxylated fatty acid derivative, or a mixture thereof comprising glycerol monohydroxystearate;
   (e) an oil carrier comprising caprylic/capric triglyceride, high oleic sunflower seed oil, octylhydroxystearate, mineral oil, or a mixture thereof; and
   (f) water,
   the composition being an emulsion comprising from 0.1 to 1.5% by weight ethyl ester of fish oil.

2. The composition according to claim 1, wherein the composition is a lotion or cream.

3. The composition according to claim 1, wherein the radical scavenger further comprises rosemary extract, octadecyl 3-(2,5-di-tert-butyl-4-hydroxyphenyl) propionate or a mixture thereof.

4. The composition according to claim 3, wherein the radical scavenger is present at an amount from 0.01 to 1.0% by weight.

5. The composition according to claim 1, wherein the peroxide decomposer is present at an amount from 0.01 to 1.0% by weight.

6. The composition according to claim 1, wherein the composition further comprises a hydroxylated fatty acid derivative which is hydroxystearyl glucoside, ethyleneglycol monohydroxystearate, glycerylmonoricinoleate, glyceryldihydroxystearate, glyceryldiricinoleate, or a mixture thereof.

7. The composition according to claim 1, wherein the composition further comprises salicylic acid.

8. The composition according to claim 1, wherein the composition is free of malodor when stored in a non-airless package.

9. The composition according to claim 1, wherein the composition further comprises fragrance and is free of malodor when topically applied.

10. The composition according to claim 1, wherein the radical scavenger is pentaerythritol tetrakis (3-3,5-di-tert-butyl-4-hydroxyphenyl) propionate).

* * * * *

UNITED STATES PATENT AND TRADEMARK OFFICE
CERTIFICATE OF CORRECTION

PATENT NO. : 10,945,945 B2
APPLICATION NO. : 16/471511
DATED : March 16, 2021
INVENTOR(S) : Marina Tomashevskaia and Hasiba Bekto It is certified that error appears in the above-identified patent and that said Letters Patent is hereby corrected as shown below:

In the Specification

At Column 4 (Line 38-39), please change "octadecyl 3-(2,5-di-tert-butyl-4-hydroxyphenyl) propionate" to read --octadecyl 3-(3,5-di-tert-butyl-4-hydroxyphenyl) propionate--.

At Column 4 (Line 61), please change "octadecyl 3-(2,5-di-tert-butyl-4-hydroxyphenyl) propionate" to read --octadecyl 3-(3,5-di-tert-butyl-4-hydroxyphenyl) propionate--.

In the Claims

At Column 12 (Line 38, Claim 3), please change "octadecyl 3-(2,5-di-tert-butyl-4-hydroxyphenyl) propionate" to read --octadecyl 3-(3,5-di-tert-butyl-4-hydroxyphenyl) propionate--.

Signed and Sealed this
Fifth Day of April, 2022

Drew Hirshfeld
*Performing the Functions and Duties of the
Under Secretary of Commerce for Intellectual Property and
Director of the United States Patent and Trademark Office*